United States Patent
Alvaro

[11] Patent Number: 6,099,312
[45] Date of Patent: Aug. 8, 2000

[54] DENTAL IMPLANT PIECE

[76] Inventor: Manuel Perona Alvaro, Eduardo Dato 19-1° dcha.-01005, Vitoria Alava, Spain

[21] Appl. No.: 09/354,013

[22] Filed: Jul. 15, 1999

[30] Foreign Application Priority Data

Jul. 18, 1998 [ES] Spain ..................................... 9801443
Apr. 13, 1999 [ES] Spain ..................................... 9900763

[51] Int. Cl.$^7$ .............................................. A61C 8/00
[52] U.S. Cl. .............................................. 433/174
[58] Field of Search .................................. 433/173, 174, 433/221, 225

[56] References Cited

U.S. PATENT DOCUMENTS

| | | | |
|---|---|---|---|
| 2,609,604 | 9/1952 | Sprague | 433/174 |
| 5,312,256 | 5/1994 | Scortecci | 433/174 |
| 5,338,197 | 8/1994 | Kwan | 433/174 |
| 5,417,692 | 5/1995 | Goble et al. | 433/174 |
| 5,470,230 | 11/1995 | Daftary et al. | 433/174 |
| 5,766,009 | 6/1998 | Jeecoat | 433/173 |
| 5,915,967 | 6/1999 | Clokie | 433/174 |

FOREIGN PATENT DOCUMENTS

| | | |
|---|---|---|
| 0636347A1 | 2/1995 | European Pat. Off. . |
| 0776639A2 | 6/1997 | European Pat. Off. . |

*Primary Examiner*—Todd E. Manahan
*Attorney, Agent, or Firm*—Ostronlenk, Faber, Gerb & Soffen, LLP

[57] ABSTRACT

An implant piece, designed for dental osseointegration implants, is made of a biocompatible material, such as titanium, and includes a body of a generally cylindrical shape, with a smooth segment with a free end that is rounded and with a threaded cylindrical segment that follows the cylindrical segment and that ends with a short cylindrical section on which the corresponding polygonal head of the implant is established. The entire length defined by both of the segments is provided with double-ruled grooves preferably equidistant from each other in its periphery. The grooves may be of uniform section or may be truncated cones. Wedges may be disposed in the grooves. The piece constitutes a mixed implant which may be placed in the patient by a simple surgical technique without perforating the sinus mucous.

13 Claims, 2 Drawing Sheets

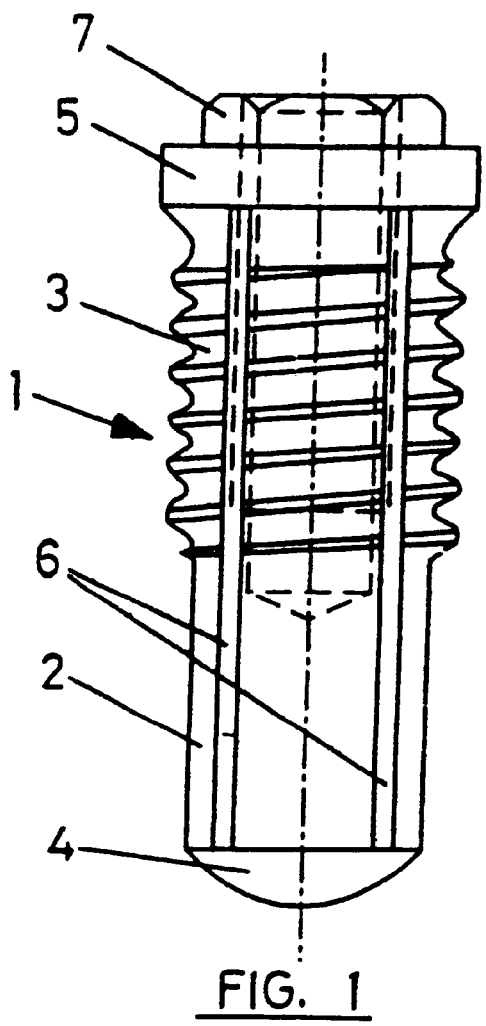
FIG. 1
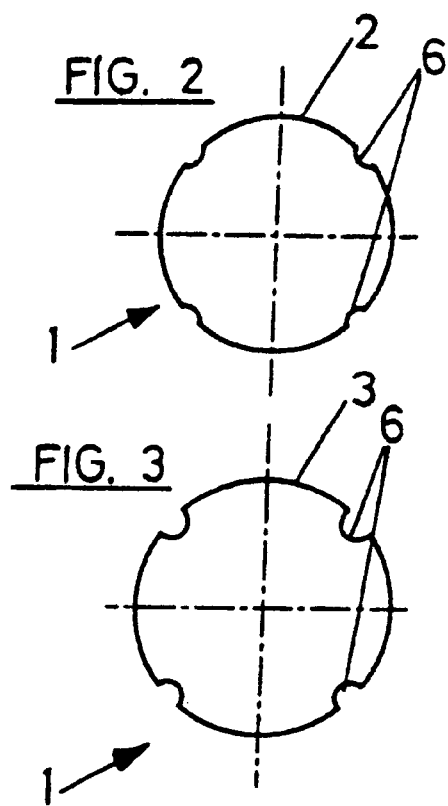
FIG. 2
FIG. 3

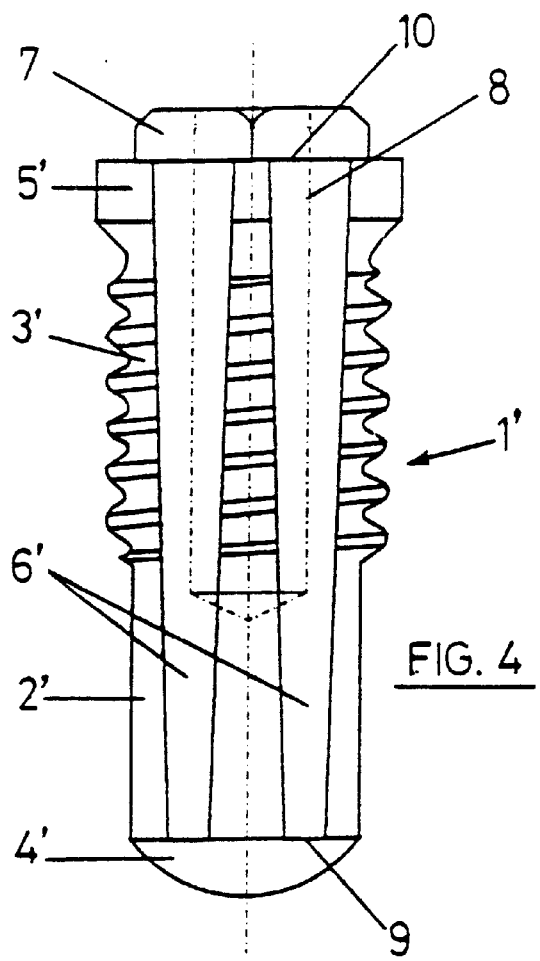
FIG. 4
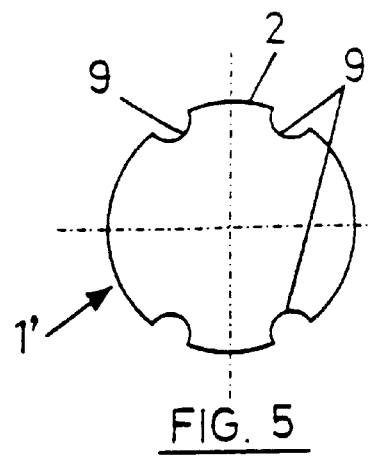
FIG. 5
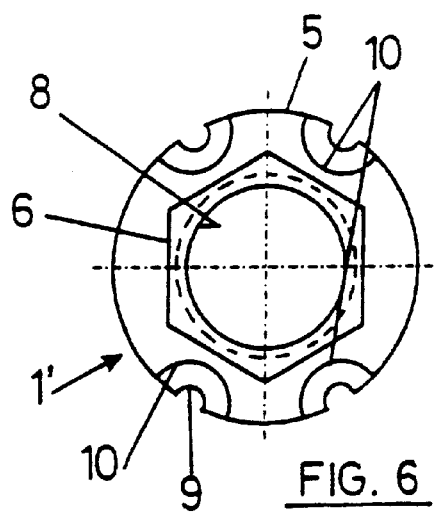
FIG. 6
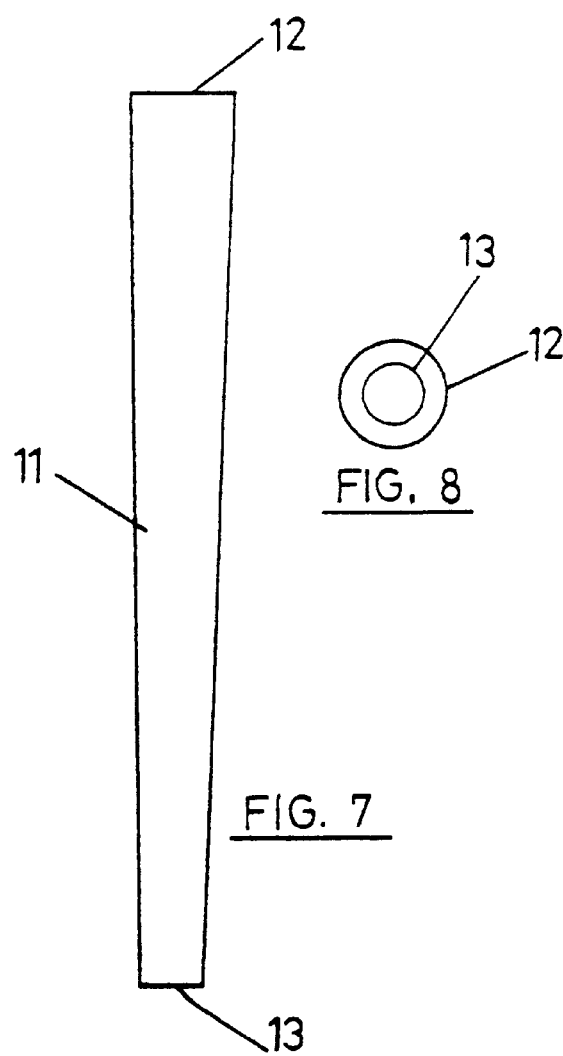
FIG. 7
FIG. 8

DENTAL IMPLANT PIECE

BACKGROUND OF THE INVENTION

The present invention relates to a dental implant piece, specifically for dental osseointegration implants, which is made of a biocompatible material, such as titanium, so that the structural properties of the implant piece allow it to be placed in areas which are not now available for conventional implants.

At present, placing osseointegrated implants in a sinus area with limited bone support leads to failure, in some cases due to a limited bone support and in other cases due to the mechanical perforation of the sinus mucous, with corresponding consequences.

Dental implants of titanium, as an example of a biocompatible material, are known. However, they are seldom used because of problems which in many cases prevent placing these implants in the upper premolar and molar areas, in relation to the maxillary sinus, especially in cases, as mentioned above, with insufficient bone thickness to place the implant.

Although there are techniques which attempt to solve this difficulty, such as elevating the sinus floor, these techniques are complex, difficult to perform and unknown to most odonto-stomatology professionals.

Two dental implant pieces are currently known. One has a cylindrical shape, which has the risk of the implant reaching the inside of the sinus cavity. The other is threaded and perforates the sinus mucous.

SUMMARY OF THE INVENTION

The object of the invention is to provide a dental implant piece which may be implanted in the bone area of the maxillary sinus of a patient by a simple surgical technique, without perforating sinus mucous, and making possible a later formation of bone under the sinus mucous around the implant, in the area within the sinus space.

The dental implant piece proposed is designed to solve this problem using a biocompatible material, e.g., titanium. The implant piece is of mixed shape, i.e., with a cylindrical segment followed longitudinally by another, coaxial and threaded segment. The cylindrical segment is at one end of the implant piece, and is finished in a rounded shape, particularly a hemisphere. The other segment, which corresponds to the head, is threaded and also cylindrical.

Along its entire length, the implant piece is provided with longitudinal grooves, preferably equidistant from each other around the piece, and in double ruling. These grooves naturally are less profound or shallower in the smooth cylindrical segment than in the threaded segment.

The threaded cylindrical segment extends toward the opposite, head end. That segment may have a cylindrical shape section above it, which section is variable in length. This allows the implant to be placed in two surgical stages, which is the normal procedure, or in a single stage. The head end is finished in a corresponding hexagonal head. Standard measures allow an exact adjustment of the transepithelial or golden cylinder in the dental prosthesis to be placed, joined to the implant. For this, a threaded space in the inner implant face is present, where a standard screw can be fitted which will support the prosthesis or the transepithelial to the implant.

The implant piece is placed by a careful technique in handling surgical drills and special instruments in order to avoid perforating the sinus mucous, which allows slow introduction of the implant up to its threaded segment. The elevation of the maxillary sinus mucous will be taken up by a blood clot from which the new bone tissue will form around the implant area, so that the intended objective is achieved.

According to a second embodiment of the invention, the axial grooves in the cylindrical body, which makes up the dental implant piece, have a truncated cone shaped, with an increasing section of the grooves from the end of the non-threaded segment to the end of the threaded segment. These grooves cross the wider area cylindrical section, which limits the threaded segment, and then the grooves are almost tangent to the faces of the polygonal head.

The construction described is completed by a set of wedges, as many wedges as there are grooves, fitted in the grooves. The wedges are truncated cones, with diameters or sections matching those of the respective grooves in which the wedges are fitted.

The wedges are introduced through the grooves of the piece, once it has been placed, to achieve a perfect attachment or fitting, both in the initial moment when they are placed and after a certain time. Thus, the invention provides an immediate loading implant. The wedges introduced through the grooves of the cylindrical piece prevent rotation of the implant.

To aid understanding of the invention, according to a preferred embodiment, a set of drawings are attached which for purposes of illustration and in a non-limiting sense show the following.

BRIEF DESCRIPTION OF THE DRAWINGS

FIG. 1 shows a side elevation view of a dental implant piece of the invention.

FIG. 2 is a cross-section showing the outline of the smooth cylindrical segment of the piece in FIG. 1, and also showing the grooves.

FIG. 3 is a cross-section showing the outline of the threaded cylindrical segment of the piece in FIG. 1, also showing the grooves.

FIG. 4 shows a side elevation of a piece for dental implants of a second embodiment of the invention.

FIG. 5 is a cross-section showing the outline of the end of the smooth segment of the cylindrical piece in FIG. 4.

FIG. 6 shows a top view of the piece of FIG. 4.

FIG. 7 is a side elevation of one of the wedges which can be fitted onto the piece of FIG. 4.

FIG. 8 is a bottom view of the wedge of FIG. 7.

DESCRIPTION OF PREFERRED EMBODIMENTS

FIGS. 1–3 show a dental osseointegration implant piece 1, made of titanium as it is a biocompatible material. It includes a cylindrical body with two longitudinally successive, coaxial segments. One segment 2 is smooth and the other segment 3 is threaded. The smooth cylindrical segment 2 has a free end 4 rounded in a hemisphere. The threaded segment 3 extends towards the opposite head end and terminates at a short length cylindrical section 5 of selected length.

The entire length of piece 1, from its end 4 to its opposite cylindrical end 5, is provided with a plurality of parallel, spaced apart, longitudinally extending, double-ruled grooves 6, equidistant from each other around the body, and with the grooves in the threaded segment 3 being deeper. As a result, the implant piece 1 is a mixed implant.

The smooth cylindrical segment 2 preferably has a length between 4 and 5 mm and a diameter between 2 and 4 mm, while the threaded cylindrical segment 3 preferably has a length between 5 and 13 mm depending on the cases, and a diameter between 2.8 and 5 mm.

The cylindrical segment 5 which corresponds to the outer end of the threaded segment 3 has a length varying between 1 and 6 mm, allowing it to be placed in two surgical stages or in a single one.

Beyond the cylindrical segment 5 there is a hexagonal head 7 of standard measures, attached on a threaded shank tightenable into a threaded bore in the piece 1, allowing an exact adjustment of the transepithelial or gold cylinder in the prosthesis to be placed and joined to the implant in question.

This new implant made of a biocompatible material (titanium) and of mixed shaped can be placed by a simple surgical technique without perforating the sinus mucous, but nevertheless allowing a later bone formation under this mucous and around the implant itself, in the area inside the sinus space.

The implant piece 1' embodiment shown in FIGS. 4–6 is also cylindrical in shape and is made of a biocompatible material, such as titanium. The piece 1' also includes a longitudinally successive smooth segment 2 followed by a coaxial threaded segment 3'. The end of the smooth segment 2' may be curved to define convex surface 4'. The threaded segment 3' ends in a cylindrical section 5 of a greater diameter and smaller height than the segment 3'. A polygonal head 7' projects out of the cylindrical section. The free end of this polygonal head 7' continues with a threaded drill or shank 8, which is used to attach the dental implant.

The surface of piece 1' has longitudinally extending grooves 6', each with a truncated cone surface. Each groove crosses the cylindrical segment 5' and ends nearly tangent to the faces of the polygonal head 7', as seen in FIG. 6.

Grooves 6' gradually increase their section from the end of smooth segment 2' to the cylindrical segment 5'. The smaller end 9 of grooves 6', is adjacent to the curved convex surface 4' which is at the end of the smooth segment 2', while the larger end 10 of grooves 6' is near or tangent to the flat faces of polygonal head 7'.

In this embodiment, the piece is completed by a number of wedges 11 as shown in FIG. 7, equal in number to the grooves 6' of piece 1'. The wedges 11 are truncated cones in shape, with the section or radius at its ends 12 and 13 matching, respectively, the maximum 10 and minimum 9 sections or radius of grooves 6'.

With this construction, once the piece 1' is placed, the full setting can be performed by placing the wedges 11 which are introduced in grooves 6' of piece 1'. These wedges may be placed at the time the piece 1' is placed, so that they are immediately locked together.

Alternatively, the piece 1' can be placed traditionally, without the wedges 11, and the wedges are later introduced only after a certain time after the implant, in case any play develops.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A dental implant piece for an osseointegration dental implant, wherein the implant piece has a cylindrical body and is comprised of a biocompatible material, the cylindrical body of the implant piece has arranged in sequence longitudinally therealong a smooth cylindrical segment followed longitudinally by a threaded surface cylindrical segment providing a threaded exterior; and the entire length of both the cylindrical and threaded segments having grooves on the exterior thereof, the grooves having a truncated cone shape wherein the section of the grooves increases, having a narrower end of the grooves at the end of the smooth cylindrical body and the grooves gradually widening and having a wider end of the grooves at the end of the threaded segment.

2. The dental implant piece of claim 1, wherein the biocompatible material is titanium.

3. The dental implant piece of claim 1, wherein the grooves are spaced equidistantly apart from each other around the cylindrical body.

4. The dental implant piece of claim 1, wherein the smooth cylindrical segment has a free end and the free end is rounded to hemispheric shape.

5. The dental implant piece of claim 1, wherein the threaded cylindrical segment has an end away from the smooth cylindrical segment and the end of the threaded cylindrical segment is extended by a shorter length cylindrical section which is not threaded.

6. The dental implant piece of claim 5, further comprising a corresponding hexagonal head being established as and above the short cylindrical section.

7. The dental implant piece of claim 5, wherein the short cylindrical section has a start at the outer end of the threaded cylindrical segment and then extends further outward away from the smooth cylindrical segment;

the grooves in the cylindrical body are defined between the end of the smooth cylinder segment and the start of the cylindrical section at the end of the threaded segment.

8. The dental implant piece of claim 7, further comprising four of the grooves in the cylindrical body.

9. The dental implant piece of claim 8, wherein the grooves are equidistant from each other around the body.

10. The dental implant piece of claim 1, further comprising four of the grooves in the cylindrical body.

11. The dental implant piece of claim 10, wherein the grooves are equidistant from each other around the body.

12. The dental implant piece of claim 1, further comprising a hexagonal head at the end of the threaded section and the hexagonal head having faces, the faces being shaped and placed and the grooves being placed so that the grooves terminate near or tangent to the faces of the polygonal head.

13. The dental implant piece of claim 1, further comprising a respective wedge in each of the grooves, and each wedge having a corresponding truncated cone shape corresponding to the section of the respective groove on which the wedge is disposed.

* * * * *